(12) United States Patent
Chu et al.

(10) Patent No.: US 7,323,450 B2
(45) Date of Patent: Jan. 29, 2008

(54) COMPLEX IMMUNO-GENE MEDICAL COMPOSITION FOR INHIBITING TUMOR CELLS

(75) Inventors: Rea-Min Chu, Taipei (TW); Ching-Yi Lin, Taipei (TW); Ya-Wen Hsiao, Taipei (TW); Kuang-Wen Liao, Taipei (TW)

(73) Assignee: National Taiwan University (TW)

( * ) Notice: Subject to any disclaimer, the term of this patent is extended or adjusted under 35 U.S.C. 154(b) by 83 days.

(21) Appl. No.: 10/798,096

(22) Filed: Mar. 11, 2004

(65) Prior Publication Data

US 2005/0203037 A1   Sep. 15, 2005

(51) Int. Cl.
*A01N 43/04*   (2006.01)
*A61K 31/70*   (2006.01)
*C07H 21/02*   (2006.01)
*C07H 21/04*   (2006.01)

(52) U.S. Cl. .................................. 514/44; 536/23.1
(58) Field of Classification Search ............... 536/23.1; 435/320.1; 514/44
See application file for complete search history.

(56) References Cited

OTHER PUBLICATIONS

Johnson-Saliba et al. (2001) Gene Therapy:optimising DNa delivery to the nucleus. Curr. Drug Targets 2:371-99.*
Verma et al., Gene therapy-promises, problems and prospects. (1997) Nature. 389:239-242.*
Shoji et al. (2004) Current Status of Delivery systems to improve Target Efficacy of Oligonucleotides. Curr. Pharm. Design 10:785-796.*
Pfeifer and Varmus (2001) Gene Therapy: Promises and Problems Annu. Rev. Genomics Hum. Genet. 2:177-211.*
Silver et al. (2000) Ly-49P Activates NK-Mediated Lysis by Recognizing H-2Dd1. J. Immunol. 165:1771-1781.*
Borrego et al. (2001) Structure and function of major histocompatibility complex (MHC) class I specific receptors expressed on human natural killer (NK) cells. Mol. Immunol. 38:637-660.*
Raulet et al. (2003) Roles of the NKG2D Immunoreceptor and its Ligands. Nature Reviews Immunol. 3:781-790.*
Perez et al. (1998) Immunohistochemical study of the local inflammatory infiltrate in spontaneous canine transmissible venereal tumour at different stages of growth. Vet. Immunol. and Immunopath. 64:133-147.*
Hsiao et al. (2002) Effect if tumor infiltrating lymphocytes on the expression of MHC molecules in canine transmissible venereal tumor cells. Vet. Immunol. and Immunopath. 87:19-27.*
Suzuki, K et al., Journal of Leukocyte Biology, 69:531-537, Apr. 2001.*
Sivori, S., et al., "Early expression of triggering receptors and regulatory role of 2B4 in human natural killer cell precursors undergoing in vitro differentiation", *PNAS*, 99(7):4526-4531 (2002).
Tan, P., et al., "Enhancement of Natural Killer Activity by an Antibody to CD44[1]", *The Journal of Immunology*, 150(3):812-820 (1993).
Storset, A.K., et al., "NKp46 defines a subset of bovine leukocytes with natural killer cell characteristics", *Eur. J. Immunol.*, 34:669-676 (2004).

* cited by examiner

*Primary Examiner*—Valarie Bertoglio
(74) *Attorney, Agent, or Firm*—Ostrolenk, Faber, Gerb & Soffen, LLP

(57) ABSTRACT

Disclosed is a complex immuno-gene medical composition for activating NK cells to enhance a host immune system. The composition includes a plurality of cytokines, including Th1 and Th2 cytokines. Th2 cytokines antagonize TGF-β inhibiting NK cells to disable the inhibition of the immune system. Th1 cytokines activate NK cells in a host to enhance the host's ability to fight against tumor cells. By use of the complex immuno-gene medical composition, removal of tumor cells is expected.

11 Claims, 9 Drawing Sheets

A

B

C ular cancer, hepatocellular carcinoma (HCC) and Meth A tumor produce TGF-β. TGF-β is capable of aiding in the growth of tumors by enhancing angiogenesis and cell adhesion. Moreover, the tumor cells evade the host immune surveillance by low MHC and low intercellular adhesion molecule-1(ICAM-1) expressions.

COMPLEX IMMUNO-GENE MEDICAL COMPOSITION FOR INHIBITING TUMOR CELLS

BACKGROUND OF THE INVENTION

1. Field of the Invention

The present invention relates to a medical composition for inhibiting tumor cell growth. In particular, it relates to a complex immuno-gene medical composition for inhibiting tumor cell growth and a method for inhibiting tumor cell growth using such medical composition.

2. The Prior Arts

Canine transmissible venereal tumor (CTVT) is a naturally occurring, poorly differentiated tumor cell. The growth of the CTVT is similar to an allograft. CTVT are transmitted in Canines by mating, biting or contacting, wherein viable tumor cells enter through injured skin or mucus.

In an experimental model, CTVT shows an expected growth pattern. The growth phases in the CTVT model include a Progressive phase (P phase), a Stasis phase (S phase), and a Regressive phase (R phase). CTVT expresses few major histocompatibility (MHC) molecules in the P phase but a large amount of transforming growth factor-β (TGF-β) in the P phase and the R phase. TGF-β is capable of inhibiting expression of MHC I and MHC II, and inhibiting activity of natural killer (NK) cells. Besides, 85% of tumor infiltrating lymphocytes (TILs) in CTVT are lymphocytes that are non-T or non-B cells, which are not able to express antigens characterized as T-cells and B-cells. From morphological observation, the aforementioned cells contain large granules in their cytoplasm similar to those found in NK cells. It is presumed that the non-T or non-B cells are NK cells.

Major histocompatibility complex (MHC) class I antigens are 44 kDa glycoproteins expressed on the cell plasma membrane associated with $\beta_2$-microglobulin ($\beta_2$m), and they are also known as histocompatibility leukocyte antigens (HLA) in humans.

Tumor cells grow by escaping the monitoring of the host immune system through many different mechanisms. One of the mechanisms used by tumor cells is a lack of or a low expression of MHC class I antigens. For example, Human tumor cells including primary breast carcinoma, advanced renal cell carcinoma, melanoma, prostate cancer, lung carcinoma, and other tumor sources from colon, bladder, skin and endometrium have been found to express low MHC levels, and some cancer cells even express no MHC. In animals, low expression of MHC is also found in T lymphoma caused by Marek's disease virus in poultry and CTVT occurring in canines.

According to the "missing self" hypothesis, when tumor cells express low or no MHC, the activating receptors on the surface of the natural killer (NK) cells in the host are activated, and the NK cells recognize and kill the target cells. However, many tumor cells secrete transforming growth factors to inhibit the cytotoxicity of NK cells. Therefore, the inability of host immune system to function normally is one of the reasons for the tumor cells to grow rapidly without much constraint.

TGF-β is a 25 kDa homodimerric protein with very potent pleiotropic regulatory effects on the mammalian immune system. Addition of exogenous TGF-β to a culture of lymphocytes decreases the proliferation of B cells, mature T cells, thymocytes, NK cells and lymphokine-activated killer (LAK) cells. Currently, It is known that many tumor cells including colorectal cancer, mammary tumor, thyreoglandu- An antagonism or reduced secretion of TGF-β is a possible way to restore the normal function of a host immune system and fight against tumor cells. Methods of immunotherapy for inhibiting TGF-β are presented herein. Administration of TGF-β antibody by injection and gene therapy with antisense oligonucleotide are the other two major methods.

T lymphocytes cannot function to kill tumor cells that secrete TGF-β or express no or low MHC. Accordingly, NK cells play important roles against tumor cells expressing no or low MHC. NK cells differentiation-related cytokines have proved to be successful in removing tumor cells. Those cytokines including γ-interferon (INF-γ), interleukin-2 (IL-2), IL-12, IL-15, IL-18 and IL-21. They are related to the functions of T lymphocytes, B lymphocytes, NK cells and other immune cells.

It is demonstrated that several cytokines are effective against tumor cells in some in vitro and animal experiments. Those researches focus upon the application of cytokines to cancer therapy. There are two kinds of cytokines that have been used against cancer cells. One kind is T-helper type 1 (Th1) cytokine, which stimulates reactions related to IL-2 and INF-γ production, and to the following cellular immunity, including IL-2, IL-12, IL-15, IL-18 and INF-γ. Another kind is T-helper type 2 (Th2) cytokine, which stimulates reactions related to production of IL-4, IL-5 and IL-6 (these three cytokines stimulate B lymphocytes to grow and differentiate), and which induces humoral immunity. However, results from those clinical researches using immuno-therapy of cytokines reveal that factors such as the method of administration, the amount administered, kinds of tumors, other additional cytokines or drugs, or potential side effects, and so on, are important in therapeutic effectivity and clinical application. Although immuno-gene-therapy is effective against tumor cells, there are limitations in its practical application for conventional methods. Usage of a combination of various cytokines according to the immune characteristics of tumor cells may be a more applicable method in the fight against tumors.

SUMMARY OF THE INVENTION

A primary object of the present invention is to provide a complex immuno-gene medical composition for inhibiting the growth of tumor cells. The composition is capable of restoring the cytotoxicity of NK cells by antagonizing the TGF-β inhibitory effect on the host immune system.

Another object of the present invention is to provide a complex immuno-gene medical composition which further activates the cytotoxicity of NK cells in a host immune system.

Some tumor cells express low MHC to escape specific attack from the host immune system (CD8+T lymphocytes) in the growth period, but the low or no expression of MCH activates NK cells. In the meanwhile, tumor cells secrete a high level of TGF-β to inhibit differentiation and activity of NK cells. Moreover, TGF-β reduces the number and inhibits the cytotoxicity of NK cells, lowers the expression of IFN-α and the α chain of the IL-2 receptor on the cellular surface, and reduces the secretion of INF-γ.

The present invention provides a complex immuno-gene medical composition according to the aforementioned mechanism used by tumor cells to evade the host immune surveillance. The composition is capable of activating the immune system by activating NK cells. The composition uses a combination of cytokines, that is, the combination of Th1 and Th2 cytokines. Th2 cytokines antagonize TGF-β inhibiting NK cells to disable the inhibition of the immune system, and Th1 cytokines activate NK cells in the host to enhance their ability to fight against tumor cells. By means of the complex immuno-gene medical composition, removal of tumor cells is expected.

The Th1 cytokines, as used herein, include IL-2, IL-12, IL15, IL-18 and INF-γ, and so on. The Th2 cytokines, as used herein, include IL-4, IL-5 and 1L-6, and so on.

To demonstrate the inhibition effect of the composition according to the present invention on tumor cells, CTVT is used as a tested tumor model. Some reasons for choosing CTVT as a tested tumor model are as follows: (1) CTVT is a type of tumor expressing low MHC; (2) CTVT produces a lot of TGF-β molecules; and (3) about 85% of tumor infiltrating lymphocytes (TIL) isolated from CTVT, expressing no CD3 and CD21, and which are not T cells or B cells, are presumed to be NK cells of canines.

Firstly, a plasmid containing human IL-6 coding sequence and another plasmid containing human IL-15 coding sequence are constructed with conventional methods, respectively. The sequences of the constructed plasmids are then confirmed. Expressed IL-6 and IL-15 is recovered after transfection in vitro and tested to evaluate the protein functionality.

Also, the restoration of the cytotoxicity of NK cells in vitro is examined by using IL-6 and IL-15 together or individually. In vivo, the expression of IL-6 and IL-15, the distribution of lymphocytes in the spleen and the cytotoxicity of NK cells are evaluated after introducing a constructed plasmid of IL-6 and IL-15 into BALA/c mice. The C.B-17 SCID mouse is used as an animal model for testing the effect of cytokines on NK cell function and the subsequent activity of NK cells on preventing the growth of CTVT tumor cells, because the SCID mouse has an immunologic deficiency in B and T lymphocytes, while keeping NK cells functional. The effects of the present complex immuno-gene medical composition in activating NK cells and against CTVT are evaluated.

The results of the above-described bioassays demonstrate that the medical composition of the present invention is efficient in antagonizing the TGF-β inhibitory effect on NK cells, restoring an inhibited host immune system, activating NK cells in the host, and enhancing the effectiveness of the host immune system against tumor cells. The medical composition including the combination of Th1 and Th2 cytokines acts against tumors not only by antagonizing TGF-β produced by the tumor cells exhibiting low expression of MHC, but also by taking advantage of other immune responses. The present invention provides multiple strategies to inhibit growth of tumor cells.

Having fully described the present invention, examples illustrating its practice are set forth below. These examples should not, however, be considered to limit the scope of the invention as it is contemplated that modifications will readily occur to those skilled in the art, which modifications will be within the spirit of the invention and the scope of the appended claims.

BRIEF DESCRIPTION OF THE DRAWINGS

The related drawings in connection with the detailed description of the present invention are described briefly as follows, in which.

DETAILED DESCRIPTION OF THE PREFERRED EMBODIMENT

Figure 1:
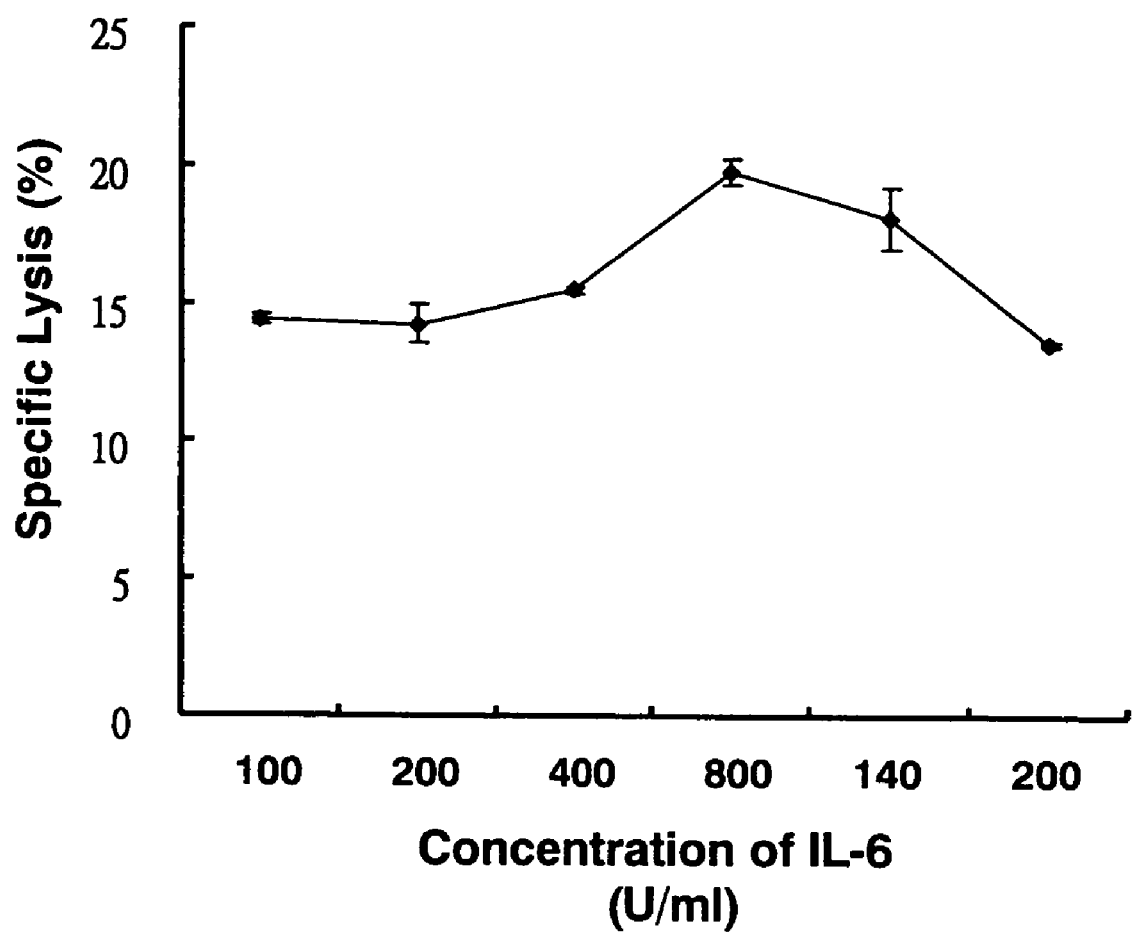
FIG. 1 shows the influence of IL-6 on the cytotoxicity of NK cells. The E/T ratio is 13/1. There are three samples in each treated group (N=3). The X-axis represents the concentration of IL-6; and the Y-axis represents the specific lysis percentage (cytotoxicity) of YAC-1 cells.

Because it is difficult to extract the IL-6 gene from the body of canines, and because there is very little IL-15 mRNA in the tissues of a normal animal body, the sequence encoding human IL-6 (SEQ. ID. NO: 1) obtained from a IL-6 plasmid and a chimeric sequence encoding human IL-15 (IL-2 SP/IL-15 MP chimeric gene, SEQ. ID. NO: 4) are used in the present invention. The chimeric sequence contains an artificial sequence encoding the signal peptide of IL-2 (SEQ. ID. NO: 2) and a sequence encoding human IL-15 (SEQ. ID. NO: 3).

A commercial pcDNA3.1/V5-His-TOPO TA Expression Kit is used to clone and construct the plasmids containing IL-6 gene and IL-2 SP/IL-15 MP chimeric gene, respectively. The constructed plasmids are transformed into E. coli cells (for example, from One shot® TOP10 competent E. coli) according to conventional methods. Also, PCR restriction enzyme cleavage and DNA sequencing are employed to confirm the sequence. The plasmids with the confirmed sequence are amplified and purified with a Nucleobond AX plasmid purification kit (Macherey-Nagel, Durën, Germany).

Conventional MTS testing is carried out to determine the activity of IL-6 in supernatant after transfection. The cell line of TF-1 (ATCC No. CRL-2003) which is dependent on IL-6 as a growth factor is employed to check the biological function of the IL-6 expressed by the constructed IL-6 plasmid. The supernatant obtained after tranfection of the constructed IL-6 plasmid into Balb/3T3 cells (ATCC No. CCL-163) stimulates proliferation of TF-1 cells. There is no stimulating activity in the supernatant obtained from a transfection of the pcDNA3.1/V5-His-TOPO vector into Balb/3T3 cells (ATCC No. CCL-163) or Balb/3T3 cells cultured alone. The result demonstrates that the constructed IL-6 plasmid expresses IL-6 protein having a biological function.

The method for evaluating the biological function of IL-15 expressed by constructed IL-15 is similar to the above method, but the cell line of TF-1 is replaced by HT-2 (ATCC No. CRL-2003) which is dependent on IL-15 as a factor for cell proliferation. The supernatant obtained from the culture of Balb/3T3 cells after transfection of constructed IL-15 plasmid is added into the culture of HT-2 cells. The supernatant obtained after transfection of the constructed IL-6 plasmid into Balb/3T3 cells stimulates proliferation of HT-2 cells. There is no stimulating activity in the supernatant obtained after transfection of the pcDNA3.1/V5-His-TOPO vector into Balb/3T3 cells or Balb/3T3 cells cultured alone. The result demonstrates that the constructed IL-15 plasmid expresses IL-15 protein having a biological function.

Moreover, the effects of IL-6 and IL-15 on antagonizing the TGF-β inhibitory activity of NK cells are examined in vitro. Compared to the usage of either IL-6 or IL-15 alone, there is higher cytotocicity to YAC-1 mice lymphoma cells when IL-6 and IL-15 are used together. The result reveals that the usage of IL-6 alone recovers the function of NK cells inhibited by TGF-β, but IL-6 alone is not capable of activating NK cells and thus, the effect on cytotoxicity is limited. In the same way, the usage of IL-15 alone can activate NK cells, but it cannot remove TGF-β. Therefore, the activity of NK cells is inhibited and cannot be restored completely. Using IL-6 and IL-15 together provides IL-6 to antagonize TGF-β inhibiting the immunity of NK cells, as well as IL-15 to activate NK cells. The cytotoxicity of NK cells is elevated effectively through the combined usage of IL-6 and IL-15.

For evidencing the effect of the combined usage of IL-6 and IL-15 plasmids, the constructed IL-6 and IL-15 plasmids are muscle electroporated alone or together into the body of BALB/c mice in vivo, and the splenocytes of the BALB/c mice are examined. The method of muscle electroporation has recently been widely used in non-viral vector delivery in gene therapy. Compared to viral vectors, the non-viral vectors are preferred because the advantages they provide include high safety, low immune response, good efficiency in plasmid delivery, good protein expression, and proximity to the body surface to enable easy operation. The results from ELISA show that expressions of IL-6 and IL-15 in host mice are successful.

Fourteen days after muscle electroporation, the numbers and cytotoxicity of NK cells in the treated mice spleens are elevated more obviously when the IL-6 and IL-15 plasmids is used together than when either the IL-6 plasmid or the IL-15 plasmid are used alone. Moreover, the numbers and cytotoxicity of NK cells, when using IL-15 plasmid alone at E/T ratio of 50/1 and 12.5/1, are lower than when using the IL-6 and IL-15 plasmids together, but higher than in usage of IL-6 plasmid alone and in usage of vector. This result reveals that IL-15 by itself is capable of enhancing the activation of NK cells.

The C.B-17 SCID mouse is an artificial breeding strain having an immunodeficiency. The mouse has no mature T cells and no B cells with normal functionality, but it has normal myeloid cells, antigen-presenting cells (APCs) and NK cells. The mice are inoculated with CTVT for xenotransplantation. Muscle electroporation is carried out to deliver IL-6 and IL-15 plasmids into the mice bodies. First, the influences of IL-6 and IL-15 on tumor establishment are evaluated. Secondly, the inhibiting effects of the two cytokines against established tumors are also evaluated. The experimental results demonstrate that combined usage of IL-6 and IL-15 plasmid is most effective in inhibiting the establishment of the tumor, and IL-15 plasmid alone is not very effective in inhibiting tumor establishment. No obvious influence due to the usage of IL-6 plasmid alone is observed. In addition, only the combined usage of IL-6 and IL-15 plasmid is effective to reduce the growth rate of the established CTVT. IL-6 plasmid or IL-15 plasmid alone cannot suppress the growth of an established tumor. In another experiment, anti-asialo GM-1 antibodies, an i.e., antibody that blocks the function of NK cells, is intraperitoneally injected into the SCID mice that carry the tumor. Then, the combined composition of IL-6 and IL-15 plasmid is delivered into the mice. This combined composition cannot suppress the growth of CTVT. The result reveals that NK cells play an important role in such method of complex immuno-gene therapy.

Example 1

Preparation and Synthesis of IL-6 and IL-15 Genes

According to the mRNA sequence encoding human IL-6, Accession No. NM_000600 from Genbank, NCBI pubmed (http://www.ncbi.nlm.nih.gov), the IL-6 gene containing 636 bases (the sequence from the base 63 to 698 is SEQ ID NO: 1) in its whole length is amplified and obtained with conventional methods.

The sequence encoding human IL-2 signal peptide (IL-2SP, 60 base, base 461 to 107, SEQ ID NO: 2) is linked to the sequence encoding human IL-15 mature peptide (IL-15 MP, 342 base, base 461 to 802, SEQ ID NO: 3) to form a IL-2 SP/IL-15 MP chimeric gene (SEQ ID NO: 4) according to the design presented by Kazuhiro et al. (2001). The design overcomes the disadvantage that it operates via multiple regulators in transcription and translation and leads to low production of IL-15 protein. In amplification, the sense strand of chimeric gene sequence is synthesized with 13 primers, which primers are from the chimeric gene sequence, total length of 402 bases, fractionated every 30 bases from the direction of 5' end. The antisense strand is synthesized with another 13 primers as the linked bridges, which sequences are complemented to the last and the next sense strain with 15 bases after the 15th base from the starting base.

The human IL-6 coding sequence is obtained from a PCR product amplified and purified from a IL-6 plasmid (from National Taiwan University College of Medicine, Taipei, Taiwan) which is created by inserting a human IL-6 gene into pcDNA3. The human IL-2SP/IL-15 MP chimeric gene is obtained from a PCR product amplified with the aforementioned 26 primers and purified. The sequences of primers in the antisense strand are complemented to the last and next sense strain with 15 bases. The primer anneals to the sequence complementary to its own sequence in the reaction with DNA polymerase to form a template. The product of IL-2SP/IL-15 MP chimeric gene is obtained from a PCR reaction.

Example 2

Cytotoxicity Evaluation of NK Cells in Mouse Spleen In Vitro

The BALB/c mice, aged 6 to 8 weeks, are sacrificed and the spleens are taken. The spleens are homogenized in RPMI-1640 medium to obtain a single cell suspension. The cell suspension is centrifuged at 1,500 rpm and 4° C. for 10 minutes. After discarding the supernatant, the cell pellets are added into 5 ml of 1×ACK lysis buffer (10×ACK lysis buffer contains 0.15 M $NH_4Cl$, 1.0 mM $KHCO_3$, 0.1 mM $Na_2EDTA$) to lyse red blood cells for 5 minutes at room temperature. The cell lysate is added into 10 ml of RPMI-1640 medium, centrifuged at 1,500 rpm and 4° C. for 10 minutes. After discarding the supernatant, the cells are rinsed once with RPMI-1640 medium. The cells are counted and diluted in LAK medium which is RPMI-10 medium containing 50 μM 2-mercaptoethanol and IL-2. The ratio of IL-2 to cells is 500 U to $1×10^6$ viable cells. The Cell solution is cultured with $2×10^6$ cells/2 ml per well in culture 24 well-plate at 37° C. for 4 to 6 days in a 5% $CO_2$ incubator. 3 days after culturing, IL-2 is again added into the culture in a ratio of 500 U to $1×10^6$ viable cells. To evaluate the influence of IL-6, IL-15, or TGF-β on the cytotoxicity of NK cells of mice splenocytes, the method for culturing of spleen cells is in accordance with the above description but the lymphokine is replaced by the cytokine of interest.

YAC-1 lymphoma cells (ATCC No. TIB-160) from mice are rinsed with PRMI-1640 medium twice with centrifugation at 1,500 rpm and 4° C. for 10 minutes, and counted using the Trypan Blue Exclusion Test. The cells are suspended in PRMI-1640 medium with $5×10^5$ viable cells/ml, and the cell numbers are determined with effector cells. The fluorescence dye of 3,3'-dioctadecyloxacarbocyanine (DIOC 18, Sigma, Mo., USA) is added into the cell suspension in a ratio of 10 μl to $5×10^5$ viable cells/ml, and incubated at 37° C. for 16 hours in a 5% $CO_2$ incubator for reaction. After rinsing twice with centrifugation at 1,500 rpm and 4° C. for 10 minutes, the cells are suspended into an RPMI-10 medium.

The splenocytes and YAC-1 cells, treated as mentioned herein, are mixed in various Effector/Target ratios (E/T ratio), 50/1, 25/1, 12.5/1, 6.25/1, 3.125/1 and added into the round bottom wells of a 96 well-plate (200 μl at most per well). The mixtures are centrifuged at 1,100 rpm and 4° C. for 5 minutes, and then incubated at 37° C. for 4 hours in a 5% $CO_2$ incubator in the dark. After incubation, the cells are harvested and mixed with propidium iodine (PI) (2500 m/ml) at a volume iof 1/100 of the cell solution. The cells are analyzed with flow cytometry (FACSCalibur flow cytometer, Becton Dickinson, N.J., USA) and CellQuest software.

Figure 2:
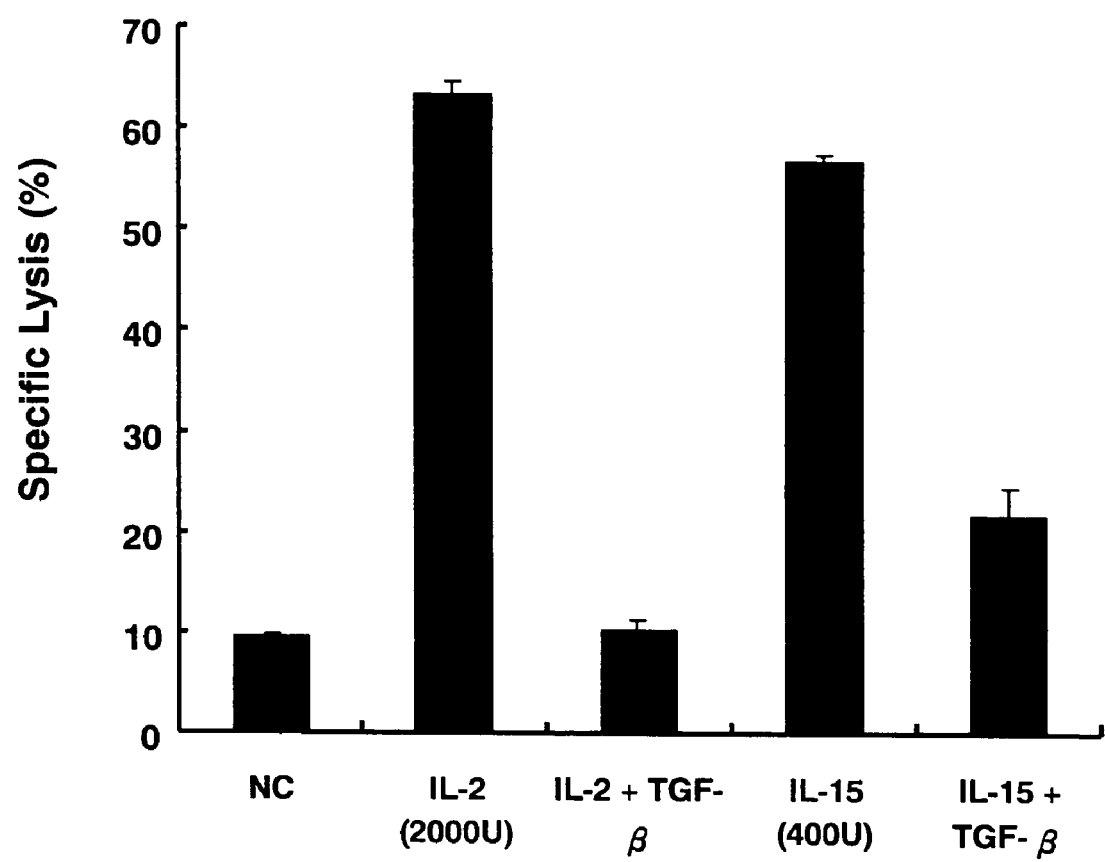
FIG. 2 compares the effect of IL-15 and IL-2 on restoring the ability of NK cellular cytotoxicity inhibited by TGF-β. The E/T ratio is 13/1. There are three samples in each treated group (N=3). The X-axis represents the groups treated; and the Y-axis represents the specific lysis percentage (cytotoxicity) of YAC-1 cells. NC is the control group without treatment of cytokines.
Figure 3:
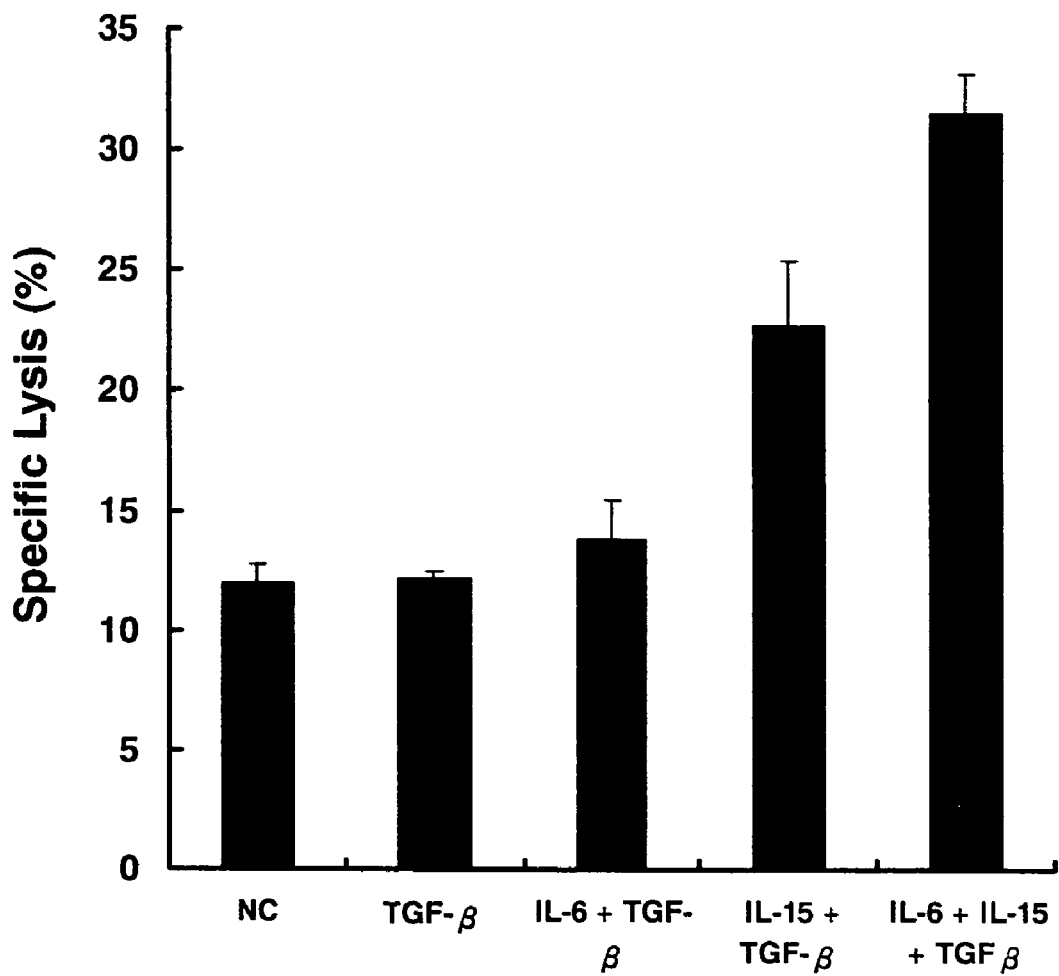
FIG. 3 shows the influence of the combined usage of IL-6 and IL-15 on NK cellular activity inhibited by TGF-β. The E/T ratio is 13/1. There are three samples in each treated group (N=3). The X-axis represents the groups treated; and the Y-axis represents the specific lysis percentage (cytotoxicity) of YAC-1 cells. NC is the control group without treatment of cytokines.

The results for IL-6 stimulating splenocytes of BALB/c mice show that the specific lysis percentage of YAC-1 lymphoma cells of mice does not increase with increased IL-6 dosage (FIG. 1). After allowing 6 days for activating splenocytes with cytokines, the specific lysis percentage in the group treated with 400U of IL-15 is similar to that of the group treated with 2000 U of IL-2. The cytotoxicity of NK cells is completely inhibited when the cells are cultured with both IL-2 and TGF-β, but only partially inhibited when cultured with IL-15 and TGF-β together. The results reveal that IL-15 is superior to IL-2 for activating NK cells, and for restoring the NK cell cytotoxicity inhibited by TGF-β (FIG. 2). Mice splenocyte culture with IL-6 and TGF-β together, with IL-15 and TGF-β or TGF-β alone, show that IL-6 is not capable of promoting cytotoxicity of NK cells, but IL-15 slowly promotes the NK cellular cytotoxicity inhibited by TGF-β. The most significant promoting effect is found when IL-6 and IL-15 are used together. (FIG. 3).

Example 3

Influence of IL-6 and IL-15 Gene Delivery with Electroporation on Cytotoxicity of NK Cells from BALB/c Mice The BALB/c mice are divided into four groups for different treatments: (1) treatment with 100 μg of pcDNA3.1/V5/His/TOPO (Mock) vector; (2) treatment with 100 μg of IL-6 plasmid; (3) treatment with 100 μg of IL-15 plasmid; and (4) treatment with 100 μg of IL-6 plasmid and 100 μg of IL-15 plasmid together. There are 6 mice in each group. The solutions for treatment such as vector, IL-6 plasmid and IL-15 plasmid solution are prepared at a concentration of 1 mg/ml with saline before electroporation.

BALA/c mice are anesthetized and each mouse is injected with 50 μl of vector or plasmid solution into both sides of a muscle, respectively. After standing for 2 minutes to diffuse the injected solution into the muscle, the mice are electroporated with an electroporator (Electro Square Porator, BTX ECM 830). tThe electroporation is carried out at 0.5 cm of inserting depth, at 100 volts for 10 times, and at 50 ms each time. After the electroporation treatments, the blood samples are taken on day 0, 3, 8, 12, 14, 15, 20, 25, 27 and 30. The blood samples are centrifuged to recover the serums and stored at −20° C.

To examine the protein expression of the IL-6 and IL-15 plasmids in vivo, the commercial ELISA kit (IL-6: Endogen, Mass., USA; IL-15: Biosource, Calif. USA) is applied to serum samples to assay the concentration of IL-6 and IL-15 with a conventional procedure.

The results demonstrate both plasmids express proteins in the mice bodies. IL-6 is detectable in serum samples in all groups, but the concentration and expression times are not in accordance. IL-15 is detectable only in groups (3) and (4).

On day 14 after electroporation, 4 mice are sacrificed for each group to collect the spleen cells and the lymphocyte subpopulations (T, B cells and NK cells) and the cytotoxcity of NK cells are evaluated.

Spleens taken from the electroporated mice are homogenized to obtain splenocytes. 100 µl splenocyte suspensions of $1 \times 10^7$ viable cells/ml are incubated with various monoclonal antibodies including rat-anti-mouse CD3-FITC antibody (Serotec, Oxford, UK), rat-anti-mouse CD19-FITC antibody (Serotec, Oxford, UK), rat-anti-mouse NK1.1-FITC antibody (PharMingen), and other isotypes. A 100 µl splenocyte solution is added into 1 µg of antibody, reacted at 4° C. for 45 minutes, and then rinsed with 1×PBS solution twice. To assess cell viability, 500 µg/ml of propidium iodine is added into the cell solution. The cell subpopulations are analyzed with flow cytometry (FACSCalibur flow cytometer, Becton Dickinson, N.J., USA).

Figure 4:
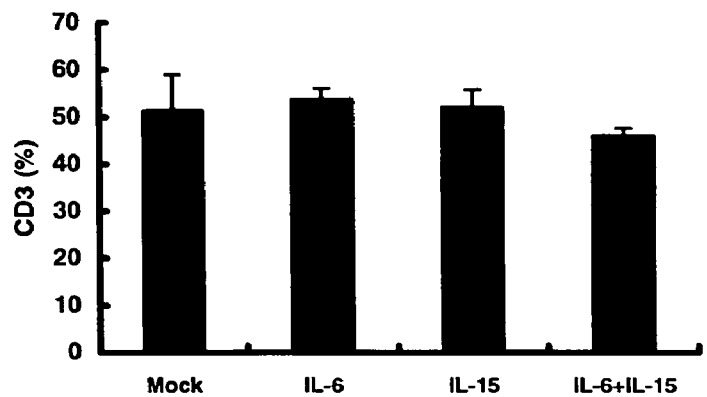
FIG. 4 shows the distribution of splenocytes after delivery of IL-6 and IL-15 plasmids into the BALB/c mice bodies via electroporation (N=3). A: Percentage of CD3+T cells in the treated groups. B: Percentage of CD19+B cells in the treated groups. C: Percentage of NK1.1+NK cells in the treated groups.
Figure 4:
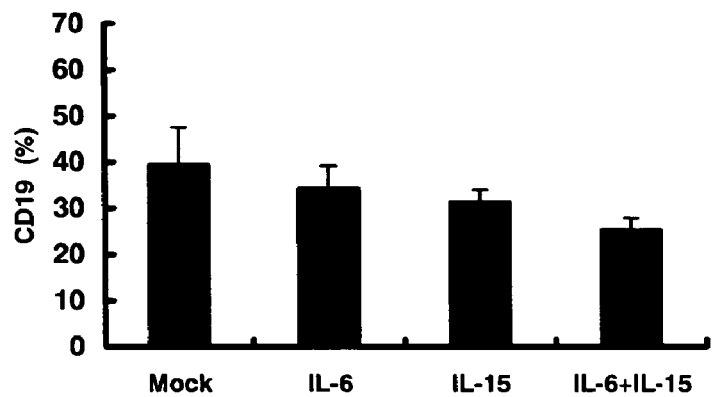
Figure 4:
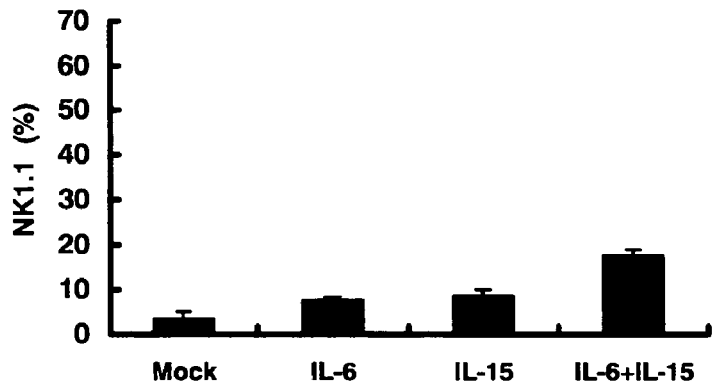
Figure 5:
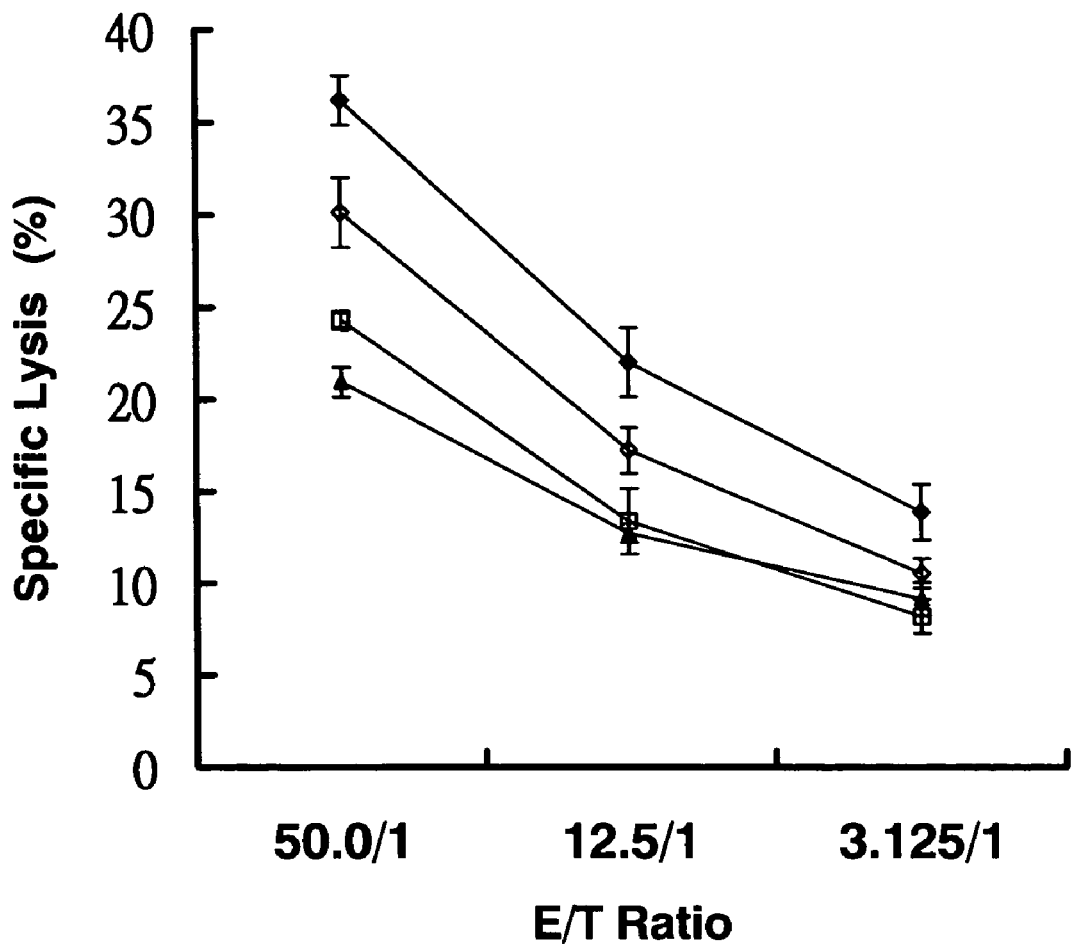
FIG. 5 shows the NK cellular cytotoxicity of splenocytes after delivery of IL-6 and IL-15 plasmids into BALB/c mice bodies via electroporation (N=4). ▲ represents the group treated with a Mock vector; □ represents the group treated with IL-6 plasmid; ◇ represents the group treated with IL-15 plasmid; black ◇ represents the group treated with both IL-6 and IL-15 plasmids; ■ represents the group treated with both IL-6 and IL-15 plasmids as well as by the administration of anti-asialo GM1 antibody.
Figure 6:
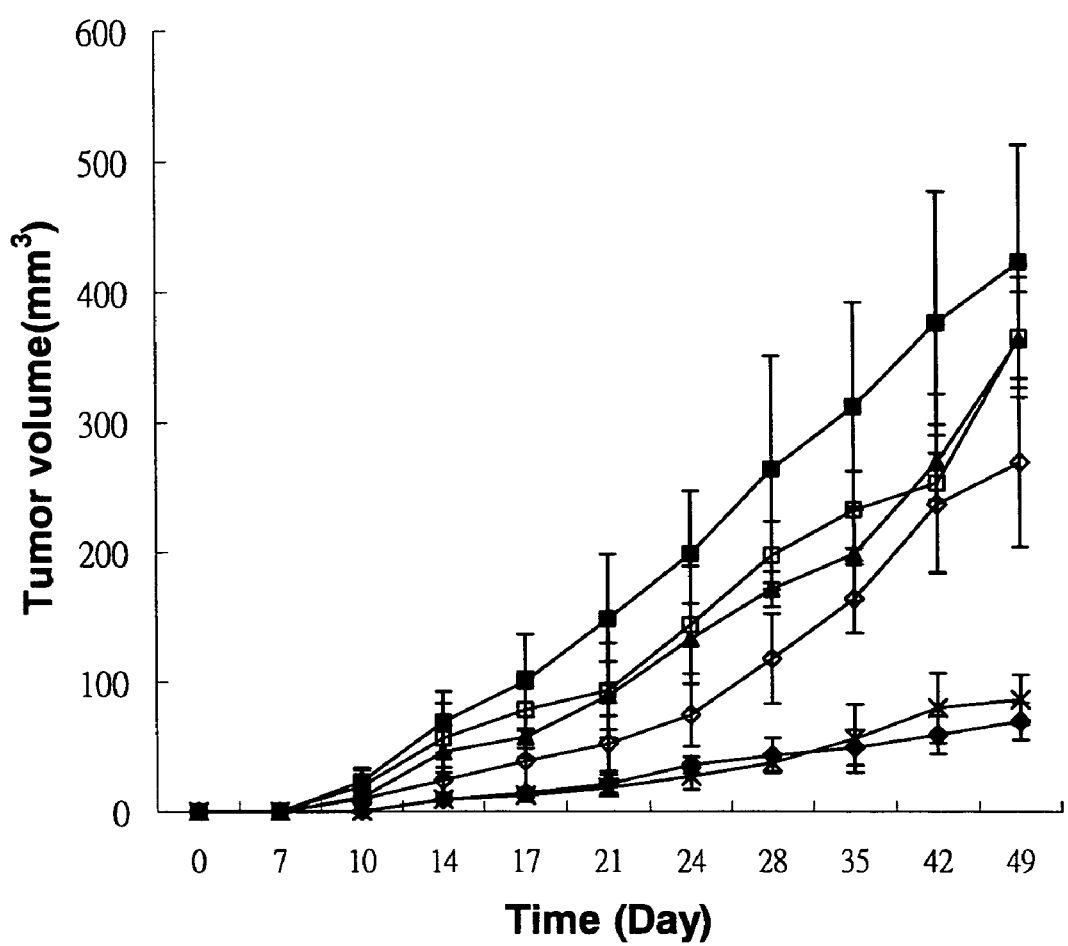
FIG. 6 shows the influence of complex immuno-gene therapy on tumor establishment of CTVT. ▲ represents the group treated with a Mock vector; □ represents the group treated with IL-6 plasmid; ◇ represents the group treated with IL-15 plasmid; black ◇ represents the group treated with both the IL-6 and the IL-15 plasmids; ■ represents the group treated with both the IL-6 and IL-15 plasmids and with anti-asialo GM1 antibody; x represents the group treated with both the IL-6 and IL-15 plasmid together as well as with administration of normal rabbit serum.

Based upon the results of the above procedure, there are no obvious differences in percentage of T cells and B cells among the four experimental groups (FIGS. 4 A and B), and the percentage of NK cells is significantly elevated in the treatment of group (4). In addition, group (4) shows superior NK cellular cytotoxicity over the other groups in whatever E/T ratios. Group (3) exhibits significantly higher cytotoxicity when the E/T ratio is 50/1 or 12.5/1, but there is no significant difference when the E/T ratio is 3.125/1. There is no significant difference between groups (1) and (2) in any E/T ratios (FIG. 5).

Example 4

Effects of Combined Usage of IL-6 and IL-15 Plasmids in Inhibiting CTVT in C.B-17 SCID Mice CTVT is surgically excised from canines inoculated artificially, homogenized and passed through a two layer stainless mesh (No. 25) to obtain a single cell suspension. CTVT cells are isolated with 42% of Percoll (Amershampharmacia biotech, NJ, USA). Vital stain (Trypan Blue Exclusion Test) is applied to determine the viability of the tumor cells. C.B-17 SCID mice are subcutaneously inoculated with $1 \times 10^8$ viable CTVT cells with an 18 G syringe on each side of the back. The size of the tumors is measured twice a week after inoculation of CTVT. The tumor size is determined according to the following formula:

$$V = \pi \times L \times W \times H/4$$

wherein, V is volume of tumor (cm$^3$), L is length of tumor (cm), W is width of tumor (cm) and H is height of tumor (cm).

Electroporation is performed on day 7 post CTVT inoculation (when the tumor is not established yet) to observe the influence of IL-6 and IL-15 on CTVT establishment. It shows that the tumors reach an observable size (diameter is about 2-3 mm) after 14 days from CTVT inoculation. In the group treated with both IL-6 and IL-15 plasmids, the tumors are obviously smaller than those found in other groups within the period of observation. The group treated with IL-15 plasmid alone shows a smaller tumor size than group treated with IL-6 plasmid alone and treated with the vector, but there is no significant difference among those treatments statistically ($p > 0.05$). Tumor growth rate in the group treated with IL-6 plasmid alone is similar to the group treated with the vector, and there is also no significant difference between the two groups.

Anti-asialo GM-1 antibody is dissolved in 1 ml of solution suitable for injection. Each mouse is intraperitoneally injected with 30 µl of the anti-asialo GM-1 antibody twice a week to block the function of NK cells, and then electroporated with IL-6 plasmid and IL-15 plasmid. The result reveals the growth rate of tumor is dramatically increased, and the tumor size is bigger than the groups subjected to other treatments.

Figure 7:
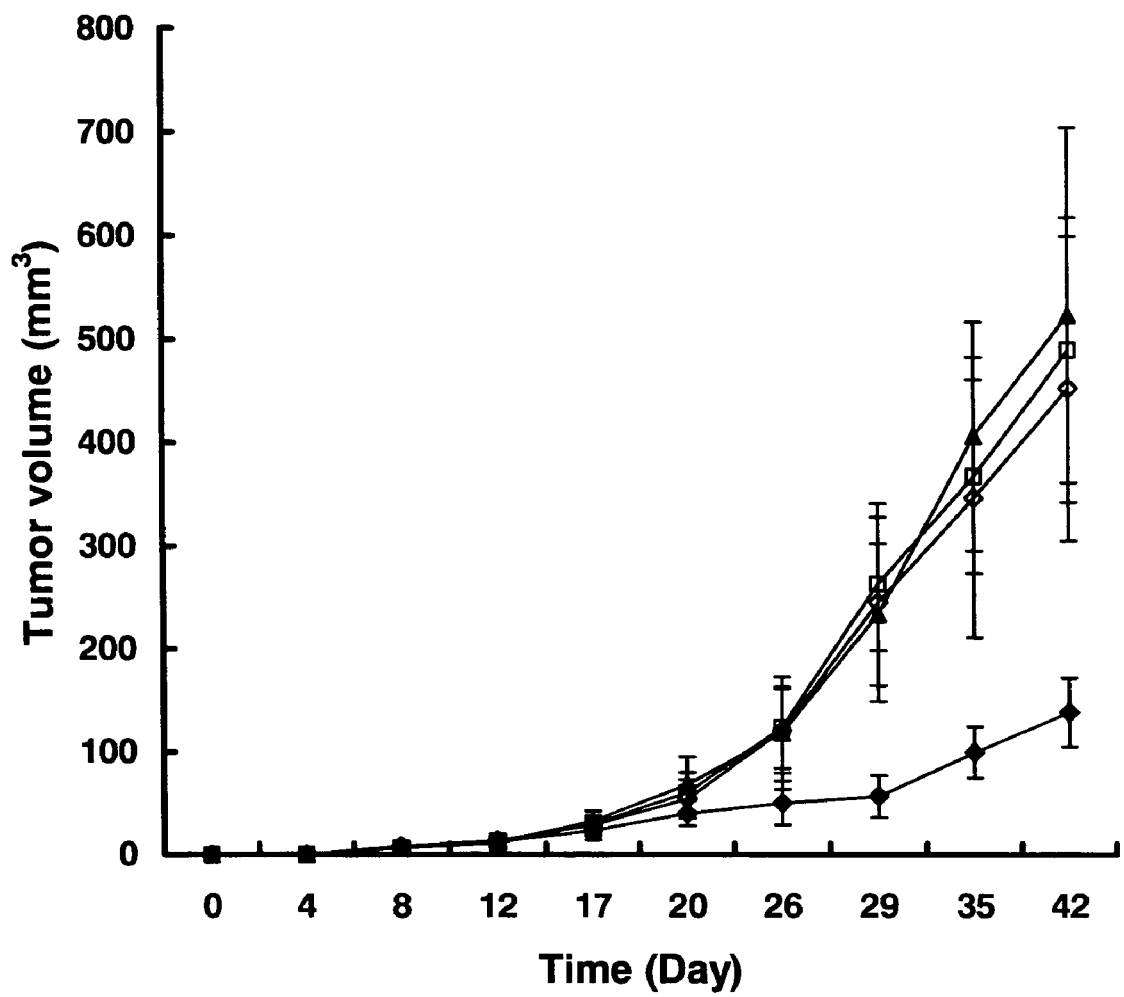
FIG. 7 shows the tumor growth curve of CTVT after therapy involving complex immuno-gene administration. There are 6 mice in each treated group (N=6). ▲ represents the group treated with a Mock vector; □ represents the group treated with IL-6 plasmid; ◇ represents the group treated with IL-15 plasmid; black ◇ represents the group treated with both the IL-6 and the IL-15 plasmids.

Additionally, C.B-17 SCID mice inoculated with CTVT cells are electroporated when the tumor reaches 5 mm. IL-6 and IL-15 together effectively delay the growth rate of established tumors. Three tumors (sample size is 6, and each mouse is inoculated on two sides) disappeared and did not grow again. In the period of observation, the average tumor size with the combined treatment (IL-6 plus IL-15) is significantly smaller than in groups treated with vector, IL-6 plasmid or IL-15 plasmid alone. IL-6 plasmid alone or IL-15 plasmid alone is not effective in inhibiting the growth of the tumors, and the sizes of tumors are similar to the group treated with vector (FIG. 7).

Figure 8:
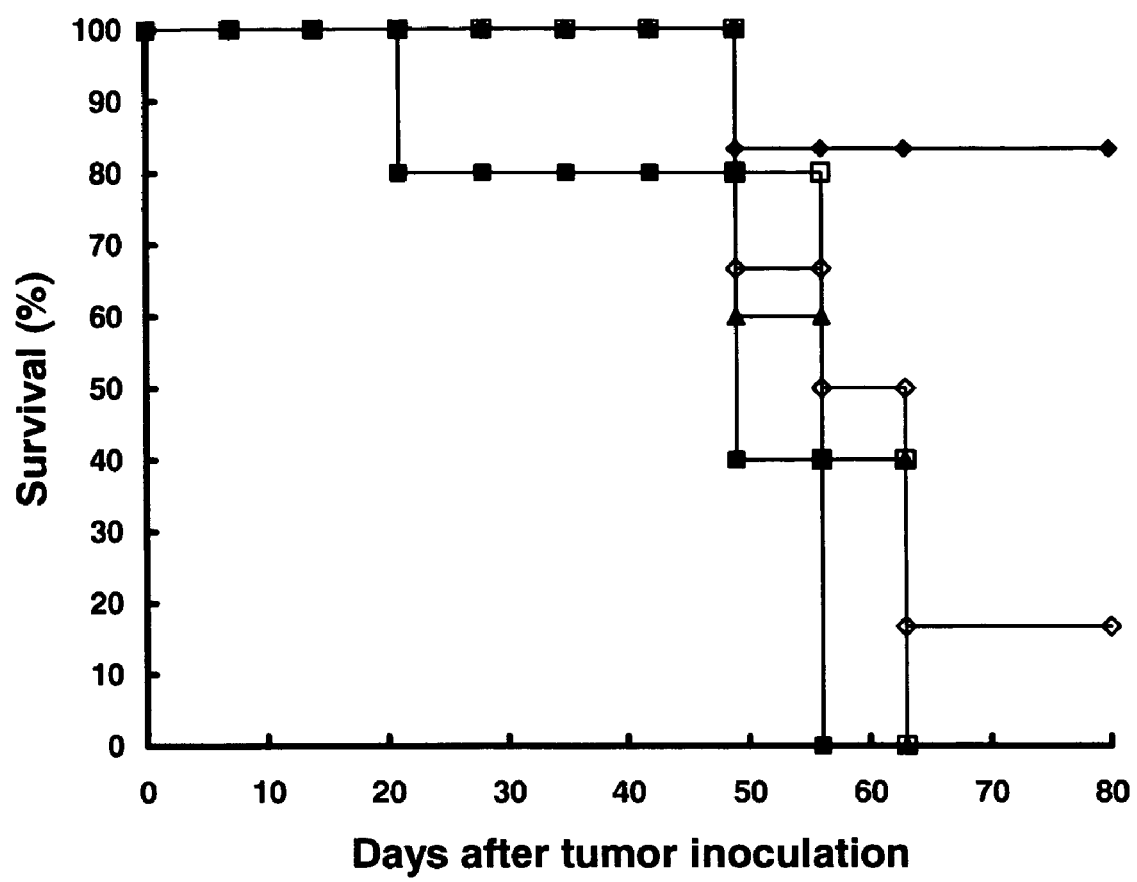
FIG. 8 shows the influence of complex immuno-gene therapy on the survival rate of mice (N=5–6). ▲ represents the group treated with a Mock vector; □ represents the group treated with IL-6 plasmid; ◇ represents the group treated with IL-15 plasmid; black ◇ represents the group treated with both the IL-6 and the IL-15 plasmids ■ represents the group treated with both the IL-6 and the IL-15 plasmids as well as with anti-asialo GM1 antibody.
Figure 9:
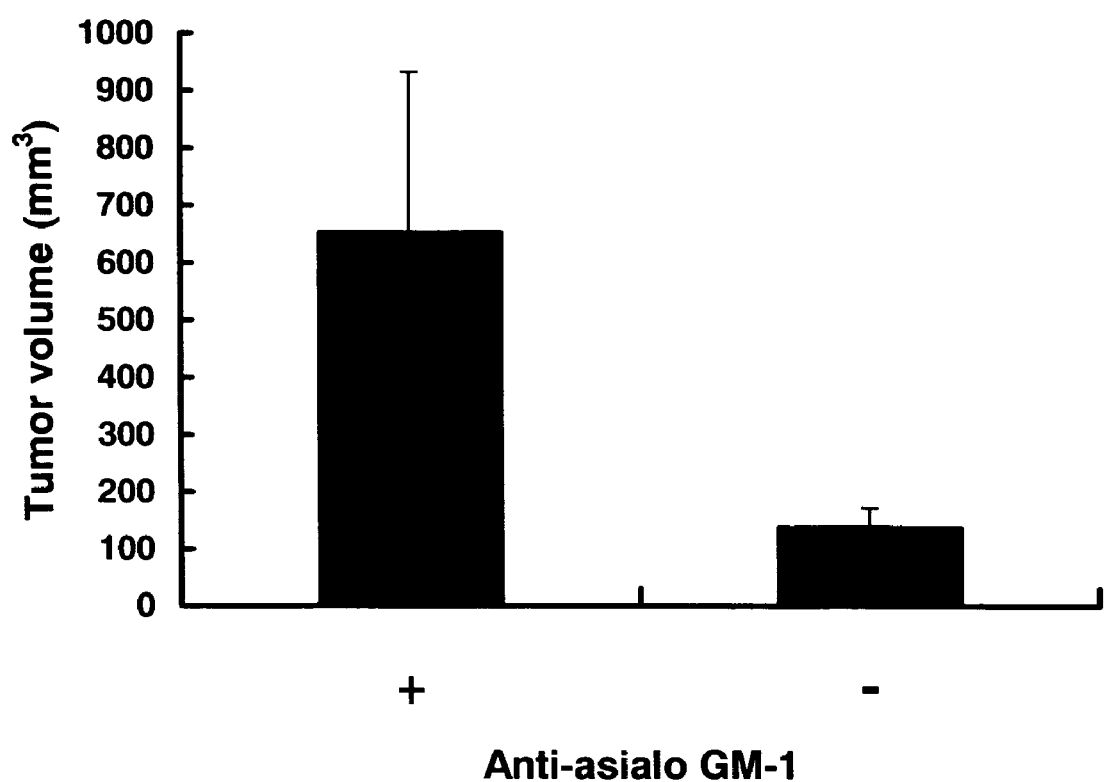
FIG. 9 shows the influence of blocking NK cellular function on the effect against CTVT tumor growth (N=6). +

Furthermore, in order to realize the relationship between tumor inhibition effect shown by combined usage of IL-6 and IL-15 plasmid, and NK cells, 4 C.B-17 SCID mice are injected peritoneally with anti-asialo GM-1 antibody to block the function of NK cells. The results show that administration of IL-6 and IL-15 plasmid in the same level mentioned above is not able to suppress growth of tumors after injection of anti-asialo GM-1 antibody, and the survival rate is increased obviously (FIG. 8 and FIG. 9). Thus, NK cells are the major cells to inhibit the growth of the tumor. IL-6 and IL-15 are effective cytokines to promote host NK activity in inhibiting the establishment of a tumor and against an established tumor.

SEQUENCE LISTING

```
<160> NUMBER OF SEQ ID NOS: 4

<210> SEQ ID NO 1
<211> LENGTH: 636
<212> TYPE: DNA
<213> ORGANISM: Human
<220> FEATURE:
```

<221> NAME/KEY: CDS
<222> LOCATION: (1)..(636)
<223> OTHER INFORMATION: IL-6

<400> SEQUENCE: 1

| | | | | | | | | | | | | | | | | |
|---|---|---|---|---|---|---|---|---|---|---|---|---|---|---|---|---|
| atg | aac | tcc | ttc | tcc | aca | agc | gcc | ttc | ggt | cca | gtt | gcc | tcc | tcc | ctg | 48 |
| Met | Asn | Ser | Phe | Ser | Thr | Ser | Ala | Phe | Gly | Pro | Val | Ala | Ser | Ser | Leu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ggg | ctg | ctc | ctg | gtg | ttg | cct | gct | gcc | ttc | cct | gcc | cca | gta | ccc | cca | 96 |
| Gly | Leu | Leu | Leu | Val | Leu | Pro | Ala | Ala | Phe | Pro | Ala | Pro | Val | Pro | Pro | |
| | | | 20 | | | | | 25 | | | | | 30 | | | |

| | | | | | | | | | | | | | | | | |
|---|---|---|---|---|---|---|---|---|---|---|---|---|---|---|---|---|
| gga | gaa | gat | tcc | aaa | gat | gta | gcc | gcc | cca | cac | aga | cag | cca | ctc | acc | 144 |
| Gly | Glu | Asp | Ser | Lys | Asp | Val | Ala | Ala | Pro | His | Arg | Gln | Pro | Leu | Thr | |
| | | | | 35 | | | | | 40 | | | | | 45 | | |

| | | | | | | | | | | | | | | | | |
|---|---|---|---|---|---|---|---|---|---|---|---|---|---|---|---|---|
| tct | tca | gaa | cga | att | gac | aaa | caa | att | cgg | tac | atc | ctc | gac | ggc | atc | 192 |
| Ser | Ser | Glu | Arg | Ile | Asp | Lys | Gln | Ile | Arg | Tyr | Ile | Leu | Asp | Gly | Ile | |
| | | 50 | | | | | 55 | | | | | 60 | | | | |

| | | | | | | | | | | | | | | | | |
|---|---|---|---|---|---|---|---|---|---|---|---|---|---|---|---|---|
| tca | gcc | ctg | aga | aag | gag | aca | tgt | aac | aag | agt | aac | atg | tgt | gaa | agc | 240 |
| Ser | Ala | Leu | Arg | Lys | Glu | Thr | Cys | Asn | Lys | Ser | Asn | Met | Cys | Glu | Ser | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| agc | aaa | gag | gca | ctg | gca | gaa | aac | aac | ctg | aac | ctt | cca | aag | atg | gct | 288 |
| Ser | Lys | Glu | Ala | Leu | Ala | Glu | Asn | Asn | Leu | Asn | Leu | Pro | Lys | Met | Ala | |
| | | | | 85 | | | | | 90 | | | | | 95 | | |

| | | | | | | | | | | | | | | | | |
|---|---|---|---|---|---|---|---|---|---|---|---|---|---|---|---|---|
| gaa | aaa | gat | gga | tgc | ttc | caa | tct | gga | ttc | aat | gag | gag | act | tgc | ctg | 336 |
| Glu | Lys | Asp | Gly | Cys | Phe | Gln | Ser | Gly | Phe | Asn | Glu | Glu | Thr | Cys | Leu | |
| | | | 100 | | | | | 105 | | | | | 110 | | | |

| | | | | | | | | | | | | | | | | |
|---|---|---|---|---|---|---|---|---|---|---|---|---|---|---|---|---|
| gtg | aaa | atc | atc | act | ggt | ctt | ttg | gag | ttt | gag | gta | tac | cta | cag | tac | 384 |
| Val | Lys | Ile | Ile | Thr | Gly | Leu | Leu | Glu | Phe | Glu | Val | Tyr | Leu | Gln | Tyr | |
| | | | | 115 | | | | | 120 | | | | | 125 | | |

| | | | | | | | | | | | | | | | | |
|---|---|---|---|---|---|---|---|---|---|---|---|---|---|---|---|---|
| ctc | cag | aac | aga | ttt | gag | agt | agt | gag | gaa | caa | gcc | aga | gct | gtg | cag | 432 |
| Leu | Gln | Asn | Arg | Phe | Glu | Ser | Ser | Glu | Glu | Gln | Ala | Arg | Ala | Val | Gln | |
| | | 130 | | | | | 135 | | | | | 140 | | | | |

| | | | | | | | | | | | | | | | | |
|---|---|---|---|---|---|---|---|---|---|---|---|---|---|---|---|---|
| atg | agt | aca | aaa | gtc | ctg | atc | cag | ttc | ctg | cag | aaa | aag | gca | aag | aat | 480 |
| Met | Ser | Thr | Lys | Val | Leu | Ile | Gln | Phe | Leu | Gln | Lys | Lys | Ala | Lys | Asn | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| cta | gat | gca | ata | acc | acc | cct | gac | cca | acc | aca | aat | gcc | agc | ctg | ctg | 528 |
| Leu | Asp | Ala | Ile | Thr | Thr | Pro | Asp | Pro | Thr | Thr | Asn | Ala | Ser | Leu | Leu | |
| | | | | 165 | | | | | 170 | | | | | 175 | | |

| | | | | | | | | | | | | | | | | |
|---|---|---|---|---|---|---|---|---|---|---|---|---|---|---|---|---|
| acg | aag | ctg | cag | gca | cag | aac | cag | tgg | ctg | cag | gac | atg | aca | act | cat | 576 |
| Thr | Lys | Leu | Gln | Ala | Gln | Asn | Gln | Trp | Leu | Gln | Asp | Met | Thr | Thr | His | |
| | | | 180 | | | | | 185 | | | | | 190 | | | |

| | | | | | | | | | | | | | | | | |
|---|---|---|---|---|---|---|---|---|---|---|---|---|---|---|---|---|
| ctc | att | ctg | cgc | agc | ttt | aag | gag | ttc | ctg | cag | tcc | agc | ctg | agg | gct | 624 |
| Leu | Ile | Leu | Arg | Ser | Phe | Lys | Glu | Phe | Leu | Gln | Ser | Ser | Leu | Arg | Ala | |
| | | | | 195 | | | | | 200 | | | | | 205 | | |

| | | | | | |
|---|---|---|---|---|---|
| ctt | cgg | caa | atg | | 636 |
| Leu | Arg | Gln | Met | | |
| | 210 | | | | |

<210> SEQ ID NO 2
<211> LENGTH: 60
<212> TYPE: DNA
<213> ORGANISM: Human
<220> FEATURE:
<221> NAME/KEY: CDS
<222> LOCATION: (1)..(60)
<223> OTHER INFORMATION: IL-2 Signal Peptide

<400> SEQUENCE: 2

| | | | | | | | | | | | | | | | | |
|---|---|---|---|---|---|---|---|---|---|---|---|---|---|---|---|---|
| atg | tac | agg | atg | caa | ctc | ctg | tct | tgc | att | gca | cta | agt | ctt | gca | ctt | 48 |
| Met | Tyr | Arg | Met | Gln | Leu | Leu | Ser | Cys | Ile | Ala | Leu | Ser | Leu | Ala | Leu | |
| 1 | | | | 5 | | | | | 10 | | | | | 15 | | |

| | | | |
|---|---|---|---|
| gtc | aca | aac | agt | 60 |

<210> SEQ ID NO 3
<211> LENGTH: 342
<212> TYPE: DNA
<213> ORGANISM: Human
<220> FEATURE:
<221> NAME/KEY: CDS
<222> LOCATION: (1)..(342)
<223> OTHER INFORMATION: Partial Sequence Encoding Human IL-15

<400> SEQUENCE: 3

```
aac tgg gtg aat gta ata agt gat ttg aaa aaa att gaa gat ctt att        48
Asn Trp Val Asn Val Ile Ser Asp Leu Lys Lys Ile Glu Asp Leu Ile
1               5                   10                  15 caa tct atg cat att gat gct act tta tat acg gaa agt gat gtt cac        96
Gln Ser Met His Ile Asp Ala Thr Leu Tyr Thr Glu Ser Asp Val His
            20                  25                  30 ccc agt tgc aaa gta aca gca atg aag tgc ttt ctc ttg gag tta caa       144
Pro Ser Cys Lys Val Thr Ala Met Lys Cys Phe Leu Leu Glu Leu Gln
        35                  40                  45 gtt att tca ctt gag tcc gga gat gca agt att cat gat aca gta gaa       192
Val Ile Ser Leu Glu Ser Gly Asp Ala Ser Ile His Asp Thr Val Glu
    50                  55                  60 aat ctg atc atc cta gca aac aac agt ttg tct tct aat ggg aat gta       240
Asn Leu Ile Ile Leu Ala Asn Asn Ser Leu Ser Ser Asn Gly Asn Val
65                  70                  75                  80 aca gaa tct gga tgc aaa gaa tgt gag gaa ctg gag gaa aaa aat att       288
Thr Glu Ser Gly Cys Lys Glu Cys Glu Glu Leu Glu Glu Lys Asn Ile
                85                  90                  95 aaa gaa ttt ttg cag agt ttt gta cat att gtc caa atg ttc atc aac       336
Lys Glu Phe Leu Gln Ser Phe Val His Ile Val Gln Met Phe Ile Asn
            100                 105                 110 act tct                                                               342
Thr Ser
```

<210> SEQ ID NO 4
<211> LENGTH: 402
<212> TYPE: DNA
<213> ORGANISM: Artificial
<220> FEATURE:
<221> NAME/KEY: CDS
<222> LOCATION: (1)..(402)
<223> OTHER INFORMATION: Bases 1-60 Code for IL-2 Signal Peptide

<400> SEQUENCE: 4

```
atg tac agg atg caa ctc ctg tct tgc att gca cta agt ctt gca ctt        48
Met Tyr Arg Met Gln Leu Leu Ser Cys Ile Ala Leu Ser Leu Ala Leu
1               5                   10                  15 gtc aca aac agt aac tgg gtg aat gta ata agt gat ttg aaa aaa att        96
Val Thr Asn Ser Asn Trp Val Asn Val Ile Ser Asp Leu Lys Lys Ile
            20                  25                  30 gaa gat ctt att caa tct atg cat att gat gct act tta tat acg gaa       144
Glu Asp Leu Ile Gln Ser Met His Ile Asp Ala Thr Leu Tyr Thr Glu
        35                  40                  45 agt gat gtt cac ccc agt tgc aaa gta aca gca atg aag tgc ttt ctc       192
Ser Asp Val His Pro Ser Cys Lys Val Thr Ala Met Lys Cys Phe Leu
    50                  55                  60 ttg gag tta caa gtt att tca ctt gag tcc gga gat gca agt att cat       240
Leu Glu Leu Gln Val Ile Ser Leu Glu Ser Gly Asp Ala Ser Ile His
65                  70                  75                  80 gat aca gta gaa aat ctg atc atc cta gca aac aac agt ttg tct tct       288
```

-continued

| | | | | | | | | | | | | | | |
|---|---|---|---|---|---|---|---|---|---|---|---|---|---|---|
| Asp | Thr | Val | Glu | Asn<br>85 | Leu | Ile | Ile | Leu | Ala<br>90 | Asn | Asn | Ser | Leu<br>95 | Ser | Ser |

| aat | ggg | aat | gta | aca | gaa | tct | gga | tgc | aaa | gaa | tgt | gag | gaa | ctg | gag | 336 |
|---|---|---|---|---|---|---|---|---|---|---|---|---|---|---|---|---|
| Asn | Gly | Asn | Val<br>100 | Thr | Glu | Ser | Gly | Cys<br>105 | Lys | Glu | Cys | Glu | Glu<br>110 | Leu | Glu | |

| gaa | aaa | aat | att | aaa | gaa | ttt | ttg | cag | agt | ttt | gta | cat | att | gtc | caa | 384 |
|---|---|---|---|---|---|---|---|---|---|---|---|---|---|---|---|---|
| Glu | Lys | Asn<br>115 | Ile | Lys | Glu | Phe | Leu<br>120 | Gln | Ser | Phe | Val | His<br>125 | Ile | Val | Gln | |

| atg | ttc | atc | aac | act | tct | 402 |
|---|---|---|---|---|---|---|
| Met | Phe<br>130 | Ile | Asn | Thr | Ser | |

What is claimed is:

1. A complex immuno-gene medical composition for inhibiting growth of tumor cells producing TGF-β comprising a therapeutically effective amount of a plasmid comprising the DNA sequence of SEQ ID NO: 1 encoding IL-6 and a therapeutically effective amount of the plasmid comprising the DNA sequence of SEQ ID NO: 4 encoding IL-15 fused to an IL-2 signal peptide.

2. The medical composition of claim 1, wherein the tumor cells express low or no MHC.

3. The medical composition of claim 1, wherein the composition inhibits the tumor cells by antagonizing TGF-β and enhancing cytotoxicity of NK cells.

4. The medical composition of claim 1, wherein the tumor is CTVT.

5. The medical composition of claim 1, wherein the plasmid is a pcDNA3.1/V5-His-TOPO vector.

6. A method for inhibiting growth of tumor cells producing TGF-β, comprising administrating a therapeutically effective amount of a complex immuno-gene medical composition to an individual in need thereof to activate NK cells and enhance cytotoxicity of the NK cells, wherein the complex immuno-gene medical composition comprises a plasmid comprising a pcDNA3.1/V5-His-TOPO vector into which is ligated the DNA sequence of SEQ ID NO: 1 encoding IL-6 and a plasmid comprising a pcDNA3.1/V5-His-TOPO vector into which is ligated the DNA sequence of SEQ ID NO: 4 encoding IL-15 fused to an IL-2 signal peptide, and wherein the medical composition is administered by muscle electroporation in vivo.

7. The method of claim 6, wherein the tumor cells express low or no MHC.

8. The method of claim 6, wherein the tumor is CTVT.

9. The method of claim 6, wherein the individual is a mammal.

10. The method of claim 6, wherein the individual is a canine.

11. The method of claim 6, wherein the individual is a rodent.

* * * * *